US005585113A

United States Patent [19]

Korsch

[11] Patent Number: 5,585,113

[45] Date of Patent: Dec. 17, 1996

[54] PROCESS FOR QUALITY CONTROL IN THE PRODUCTION OF TABLETS BY PRESSING

[75] Inventor: Wolfgang Korsch, Berlin, Germany

[73] Assignee: Korsch Pressen GmbH, Berlin, Germany

[21] Appl. No.: 303,414

[22] Filed: Sep. 9, 1994

[51] Int. Cl.[6] ........ A61K 9/20

[52] U.S. Cl. ........ 424/464; 424/465

[58] Field of Search ........ 424/465, 464; 364/476; 425/135

[56] References Cited

U.S. PATENT DOCUMENTS

| | | | |
|---|---|---|---|
| 4,100,598 | 7/1978 | Stiel et al. | 364/476 |
| 4,570,229 | 2/1986 | Breen et al. | 364/476 |
| 5,186,956 | 2/1993 | Tanino et al. | 425/135 |

FOREIGN PATENT DOCUMENTS

| | | |
|---|---|---|
| A-2252917 | 6/1975 | France . |
| A-2607441 | 6/1988 | France . |
| 61-111799A | 5/1986 | Japan . |

OTHER PUBLICATIONS copy of European Search Report dated Jan. 25, 1995.

Dipl.-Ing. Wolfgang Korsch, Emil Korsch oHG, Maschinenfabrik, Roedernallee 88–90, D-1000 Berlin, Separatdruck aus "Swiss Pharma" 2 (1980) nr. 4, 28–33.

*Primary Examiner*—Thurman K. Page
*Assistant Examiner*—William E. Benston, Jr.
*Attorney, Agent, or Firm*—McGlew And Tuttle, P.C.

[57] ABSTRACT

A process for quality control in tablet production by pressing by means of influencing the pressing force, the weight, the hardness, and the height of the tablets by means of a control mechanism. The task of the invention is to develop a process of the type according to this concept, according to which all necessary control mechanisms for maintaining a constant tablet weight, tablet height, and tablet hardness operate in such a way that a rapid control of deviations is assured, and according to which, the limiting values can be optimized automatically, is hereby resolved in that the control system is divided into several influential and essentially parallel running control circuits for the simultaneous control of the pressing force as well as the tablet parameters of weight, height, and hardness.

14 Claims, 1 Drawing Sheet

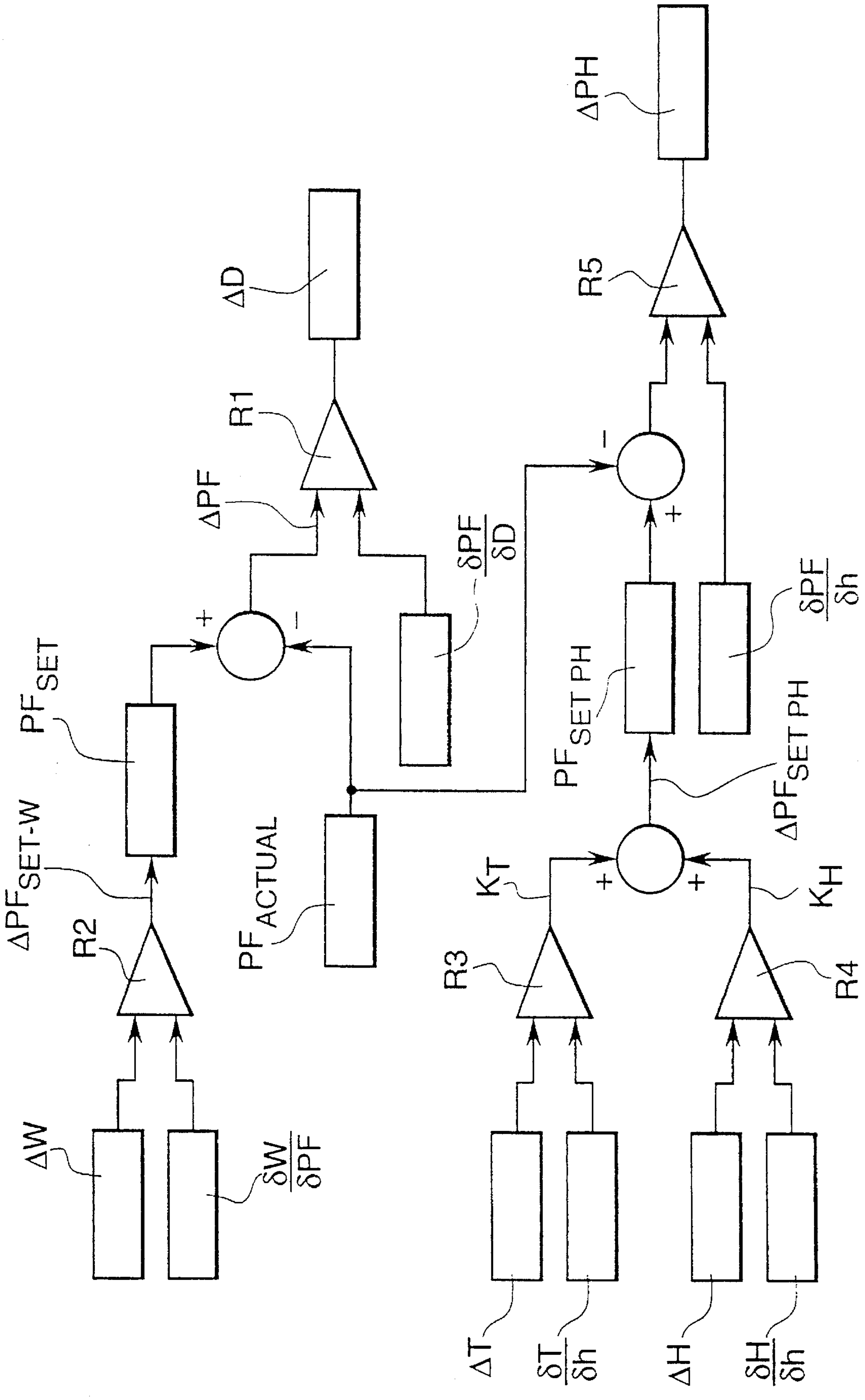
ΔW
δW/δPF
R2
ΔPF SET-W
PF SET
PF ACTUAL
ΔPF
R1
ΔD
δPF/δD
ΔT
δT/δh
ΔH
δH/δh
R3
R4
K T
K H
ΔPF SET PH
PF SET PH
δPF/δh
R5
ΔPH

PROCESS FOR QUALITY CONTROL IN THE PRODUCTION OF TABLETS BY PRESSING

FIELD OF THE INVENTION

The invention concerns a process for quality control in tablet production by pressing including structure for changing the pressing force, the weight of the resulting tablet, the hardness of the resulting tablet and the height of the resulting tablet using a control mechanism.

BACKGROUND OF THE INVENTION

An important quality parameter for tablet production is maintaining the pregiven tablet weight, which, with sufficient mixing material assures maintaining the limits for the content of the active ingredient. The basis for any automatic control of a tabletting machine is the relationship between measured maximum pressing force of a tablet and the mass of the material filled into the mold (tablet weight). There exists, therefore, a direct relationship between the tablet weight and the pressing force necessary for production of controlled tablets. This relationship is utilized for the application of automatic monitoring and control equipment on rotary tabletting presses. A specific pressing force is assigned to each tablet weight for a tablet shape given in advance by the pressing tool and an established tablet height, as a function of the material to be pressed. If the quantity filled and therefore the tablet weight fluctuates with a constant tablet height, there is a change in pressing force resulting directly from this.

It is already known to monitor the established tablet weight by means of a computer-controlled fully electronically operating PID control (proportional-integral-differential control) via the mean value of pressing forces, which is determined from the individual sequential pressings (Korsch, Wolfgang: "Drug control—The new computer-controlled press force monitoring device for fully automatic tablet weight regulation on rotary presses" in the journal "Swiss Pharma" 2 (1980) No. 4, pp. 28–33). During automatic tablet production, the PID control continuously compares the measured pressing force with the desired pressing force. If there is a deviation between these two values, then the computer automatically determines the difference and activates the metering device, thus the desired pressing force, and the prescribed tablet weight is achieved. In addition, the parameters of weight, height, and hardness of the tablets are measured discontinuously, whereby deviations from the set values lead to establishing a new pressing-force set value. Upon fluctuations in height or hardness, the new set value for pressing force is controlled by a path height adjustment.

A process for quality control in the production of tablets is described in EP-0,261,358. According to this, samples are taken during the production of tablets, which consist of a great number of tablets, whose common weight actual value is compared with the weight set value, and in which the tabletting machine is subsequently controlled corresponding to the deviation between the actual value and the set value in order to bring the tablet weight to the set value. Prior to a subsequent control of the tabletting machine, the weights of individual tablets of the sample are measured and compared. For a determination of one or more tablets of the sample essentially deviating in weight from the set value, the statistics are corrected by a correction calculation and the corrected value is utilized for the subsequent control.

It is a disadvantage in the known method, that the parameters of weight, height, and hardness of the tablets are sequentially controlled, due to the high mutual dependencies and the very complex system. A change in the dosage not only causes a change in weight, but has effects on the hardness and the density of the tablets. Due to the individual controls that occur sequentially at large time intervals, conditioned by the system, there arises a large inertia in the control of deviations. The set value and the boundary value for the parameters must be rigidly given beforehand by the system user, which can lead to error-associated eliminating or accepting of tablets, as the case may be, when these values do not optimally correspond to the conditions.

SUMMARY AND OBJECTS OF THE INVENTION

It is an object of the invention therefore to develop a process for quality control in tablet manufacture by pressing, according to which all necessary control mechanisms for maintaining a constant tablet weight, tablet height and hardness operate such that a rapid control of deviations is assured and according to which the limiting values can be optimized automatically.

According to the invention, a process for quality control for tablet production is provided including a control system for controlling the pressing force, the weight of the resulting tablet, the hardness of the resulting tablet, the height of the resulting tablet. The process includes dividing a control system into a plurality of influencing control circuits and running the influencing control circuits in parallel for simultaneously controlling the pressing force, the tablet parameters of weight, height and hardness.

Due to the possibility of floating mean formation for pressing force, weight, height and hardness of the tablets, it is achieved that fluctuations due to the different filling ratios of the molds of the press are not determined first after determining the mean value from a large sampling and thus produce a control only at this point in time, but that tendencies of a changing value in the same direction can be determined in a timely-manner or earlier than previously possible.

The production of a correlation between pressing force and weight for each pressing station permits assigning to each individual stamping station its maximum and minimum pressing force limits. Thus it is assured that stamping variations do not lead to erroneous decisions in the tablet sorting.

A good overview of the control process is achieved by the application of a FUZZY (logic) controller. The very complex system may be completely described and in this way is made controllable. It is easily modifiable and provides an overview. The system behavior is optimally adapted to all boundary conditions. The control properties of tablet pressing are essentially improved; i.e., among other things, there is no overshoot of the control mechanism, and a control deviation to zero is achieved even after a few drum rotations. Inconsistency of the pressing material, temperature fluctuations, stochastic fluctuations of all influence quantities are controlled effortlessly by the adaptive properties of the FUZZY control mechanism.

According to further aspects of the invention, the actual pressing force is kept constant in a first controlled circuit by the influence of a change in dosage on the value of the set pressing force and a second control circuit is run in parallel with the first control circuit wherein the weight is measured and a new value for the set pressing force is calculated based on weight deviation. A dosage change is produced in the first control circuit and a weight deviation is equilibrated. In the third control circuit the height deviation of the tablet is measured and then the fourth control circuit the hardness deviation is measured. New values are calculated for the set pressing force-path height based on the new values of deviations that are present in the hardness and height. A deviation between the value of the set pressing force-path height and the value of the actual pressing force is controlled in the fifth control circuit by a path-height adjustment.

The invention is described in more detail in the following on the basis of an example of embodiment of the process, represented in the drawing, for quality control in tablet production by a modem high-power rotary press.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

BRIEF DESCRIPTION OF THE DRAWINGS

In the drawings:

The only FIGURE is a model of a control mechanism for the simultaneous control of the tablet parameters of weight, height, and hardness.

DETAILED DESCRIPTION OF THE PREFERRED EMBODIMENTS

The control system is divided into control circuits R1–R5, which are joined together such that they are connected and run in parallel. The first or dosage control circuit R1 effects a constant holding of the actual pressing force $PF_{actual}$ on the value of the set or desired pressing force $PF_{set}$ by means of a metering change ΔD. The actual pressing force $PF_{actual}$ is the rigid or floating mean of several individual pressing forces at the stamping stations of the press. The first input value on the first control circuit R1 is the value of the pressing force deviation ΔPF between the set or desired pressing force $PF_{set}$ and the actual pressing force $PF_{actual}$.

The dosage control circuit R1 is loaded with a second input quantity, which is formed by the sensitivity of the pressing force to the dosage dPF/dD. The sensitivity dPF/dD determines the accuracy of the pressing force control as a function of the change in dosage ΔD and is adapted to the control during the operation of the press, i.e., the sensitivity dPF/dD is adaptive.

Parallel to this, the weight W, the height T, and the hardness H of the tablets is continuously measured and a floating mean is calculated for each of these. Depending on the measured deviation in weight ΔW, a new value is calculated in the second control circuit R2 for the set pressing force $PF_{set}$, which again produces a dosage change ΔD in the first control circuit R1, whereby the deviation in weight ΔW is equilibrated. The change of the set pressing force $PF_{set}$ is determined by a first pressing force correction value $\Delta PF_{set\text{-}w}$. In addition, a sensitivity-weight dW/dPF is applied as a second input quantity in the second control circuit R2, which quantity determines the accuracy in weight control as a function of the change in pressing force $\Delta PF_{set\text{-}w}$. In addition, this sensitivity dW/dPF is adaptive and is adapted to the control during the tablet production process.

New values for the set pressing force-path height $PF_{set\text{-}PH}$ are calculated in control circuits R3, R4 for height and hardness deviations of the tablets. For this purpose, the values for deviation in height ΔT and for sensitivity-height dT/dh are applied to the third control circuit R3 as initial values and a height correction $K_T$ is generated. Values for deviation in hardness ΔH and sensitivity hardness dH/dh are applied at the input of the fourth control circuit R4 and a hardness correction $K_H$ is generated. The sensitivities dT/dh and dH/dh are again adaptive.

In the fifth or path height control circuit R5 a deviation between the set pressing force-path height $PF_{set\text{-}PH}$ and the actual pressing force $PF_{actual}$ is controlled by a path-height adjustment by the value ΔPH. The second input quantity at the fifth or path height control circuit R5 is the sensitivity-pressing force-path height dPF/dh with adaptive properties.

Control circuits R1 and R5 operate alternatively.

All control circuits R1 to R5 operate continuously. Actual values are continuously available due to a preferable floating mean formation individual control quantities. Control circuits R1 to R5 may also be subdivided into several partial circuits, which, e.g., have different characteristics depending on the control deviation.

The limiting values for pressing force PF, at which point the presses are stopped and/or the tablets are eliminated, are adaptively determined by determining the relationship between the pressing force PF and the weight W, the height T, and the hardness H from the data measured in the running operation. This determination may also be conducted with respect to the stamp. For pregiven limits for weight W, height T and hardness H, the respective pressing force limits can be determined from this relationship.

The description of the control system is produced on the basis of the great complexity preferably by methods of the FUZZY set theory. The technical quantities of the model for the control mechanism are "fuzzified" for this purpose by converting them into linguistic variables, e.g., weight deviation, sensitivity-weight, height deviation, etc. Terms are assigned to these linguistic variables, such as, "low, average, high", whereby these terms represent "fuzzy" quantities. The terms obtain appropriate functions, by means of which it is possible the degree of appropriateness of the individual terms for each value of the linguistic variables. For example, if a weight deviation of 5 mg fulfills the condition "average deviation" to the degree 0.2, the condition "high deviation" refers to the degree 0.7.

The linking of the variables is produced by means of FUZZY operators, such as, e.g. "minimum operator, maximum operator, gamma operator" or the like.

The processing of "fuzzy" information is produced by means of production controls, which are worked out by methods of FUZZY inference e.g., MAX-MIN/MAX-PROD inference or FAM/inference, and others. After stating all inference processes, the output variables, which now as "FUZZY values" are "defuzzified", i.e., converted into the "sharp" regulated quantities "dosage change" and "path-height change". Preferably the planar center of mass procedure is applied as the "defuzzification" method, but other methods, such as the maximum mean procedure, the maximum center of mass procedure and others are also possible.

While a specific embodiment of the invention has been shown and described in detail to illustrate the application of the principles of the invention, it will be understood that the invention may be embodied otherwise without departing from such principles.

APPENDIX
REFERENCE DENOTATION LIST

| | |
|---|---|
| R1 | Control circuit |
| R2 | Control circuit |
| R3 | Control circuit |
| R4 | Control circuit |
| R5 | Control circuit |
| PF | Pressing force |
| $PF_{actual}$ | Actual pressing force |
| $PF_{set}$ | Set pressing force |
| $\Delta PF_{set}$ | Set pressing force deviation |
| ΔD | Dosage change |
| dPF/dD | Sensitivity |
| W | Weight |
| T | Height |
| ΔT | Height deviation |
| H | Hardness |
| ΔH | Hardness deviation |
| ΔW | Weight deviation |
| dW/dPF | Sensitivity |
| dT/dH | Sensitivity |
| dH/dh | Sensitivity |
| $PF_{set-PH}$ | Set pressing force-path height |
| $\Delta PF_{set-PH}$ | Set pressing force-path height deviation |
| ΔPH | Path height deviation |

What is claimed is:

1. A process for quality control of tablet production, the process comprising the steps of:

setting a desired weight for a tablet;

measuring an actual weight of the tablet;

determining a deviation between the actual weight and the desired weight of the tablet;

forming a first pressing force correction value $\Delta PF_{set1}$ to correct said deviation in said weight of the tablet;

adjusting a first set pressing force $PF_{set1}$ by said $\Delta PF_{set1}$;

measuring an actual pressing force $PF_{actual}$;

determining a first deviation ΔPF1 between said $PF_{set1}$ and said $PF_{actual}$;

using said ΔPF1 to calculate a change in dosage of the tablet production;

determining a deviation in a height of a tablet;

forming a second pressing force correction value $\Delta PF_{set2}$ to correct said deviation in said height of the tablet;

determining a deviation in a hardness of a tablet;

forming a third pressing force correction value $\Delta PF_{set3}$ to correct said deviation in said hardness of the tablet;

combining said $\Delta PF_{set2}$ and said $\Delta PF_{set3}$ into a fourth pressing force correction value $\Delta PF_{set4}$;

adjusting a second set pressing force $PF_{set2}$ by said $\Delta PF_{set4}$; determining a second deviation ΔPF2 between said $PF_{set2}$ and said $PF_{actual}$; and using said ΔPF2 to calculate a change in path height of the tablet production.

2. A process in accordance with claim 1, wherein:

said change in dosage is calculated to maintain the weight of the tablet substantially constant and minimize ΔPF1;

said change in path height is calculated to maintain the height and hardness of the tablet substantially constant and to minimize ΔPF2;

said actual pressing force $PF_{actual}$ is a mean value which is updated for individual pressing stations at each cycle of the tablet production;

control circuits are provided for creating said first pressing force correction value $\Delta PF_{set1}$, said second pressing force correction value $\Delta PF_{set2}$, said third pressing force correction value $\Delta PF_{set3}$, said fourth pressing force correction value $\Delta PF_{set3}$, said first deviation ΔPF1, and said second deviation ΔPF2, said control circuits having adaptive sensitivities to create said correction values and said deviations;

continuously adjusting said adaptive sensitivities of said control circuits to changing behavior of the tablet production;

said change in dosage and said change in path height are performed alternatively during the tablet production.

3. A process in accordance with claim 2, wherein:

said deviations in weight, height and hardness of the tablet are determined for each of the individual pressing stations.

4. A process in accordance with claim 2, wherein:

said adaptive sensitivities are represented by change of weight with respect to a change of pressing force dW/dPF, change in height with respect to the change in path height dT/dh, change in hardness with respect to the change in path height dH/dh, change in pressing force with respect to the change in path height dPF/dh, and change in pressing force with respect to the change in dosage dPF/dD;

said adaptive sensitivities, said correction values and said deviations are all applied as inputs to said control circuits.

5. Process according to claim 2, wherein the sensitivities are adapted to controls during operation.

6. Process according to claim 2, wherein the control circuits are divided into a plurality of partial control blocks.

7. Process according to claim 2, wherein a limiting value for the pressing force is determined adaptively to values measured during running operation and a pregiven limiting value for weight, height and hardness of the tablets.

8. Process according to claim 2, further comprising applying FUZZY (logic) for description, design, realization and optimization of the control circuits.

9. A process for quality control of tablet production, the process comprising the steps of:

producing a tablet on a press with a pressing force, a dosage D, a path height of the press, a height of the tablet, and a hardness;

determining a desired pressing force for the tablet;

measuring an actual pressing force $PF_{actual}$ of the tablet in a sliding average which is updated for each tablet formed;

calculating a pressing force deviation ΔPF between said $PF_{set}$ and said $PF_{actual}$;

calculating in a dosage control circuit, a change in dosage ΔD which when added to said dosage would reduce ΔPF;

calculating in a path height control circuit a change in path height ΔPH which when added to said path height would reduce ΔPF;

determining a desired weight for the tablet;

measuring an actual weight of the tablet;

calculating a weight deviation ΔW between said desired weight and said actual weight;

calculating a first pressing force correction $\Delta PF_{set-w}$ which when added to said desired pressing force $PF_{set}$ would reduce said weight deviation ΔW;

determining a desired height for the tablet;

measuring an actual height of the tablet;

calculating a height deviation ΔT between said desired height and said actual height;

calculating a height correction $K_T$ which when added to said desired pressing force $PF_{set}$ would reduce said height deviation $\Delta T$;

determining a desired hardness for the tablet;

measuring an actual hardness of the tablet;

calculating a hardness deviation $\Delta H$ between said desired hardness and said actual hardness;

calculating a hardness correction $K_H$ which when added to said desired pressing force $PF_{set}$ would reduce said height deviation $\Delta T$;

combining said hardness correction $K_H$ and said height correction $K_T$ to form a second pressing force correction $\Delta PF_{set\text{-}PH}$ which when added to said desired pressing force $PF_{set}$ would reduce said height and hardness deviation $\Delta T$ and $\Delta H$;

A) combining said first pressing force correction $\Delta PF_{set\text{-}w}$ with said desired pressing force $PF_{set}$ to form a new desired pressing force $PF_{set}$;

calculating a new pressing force deviation $\Delta PF$ between said new desired pressing force $PF_{set}$ and said $PF_{actual}$;

operating said dosage control circuit with said new pressing force deviation $\Delta PF$ to calculate a new change in dosage $\Delta D$;

modifying said dosage by said new change in dosage $\Delta D$;

B) combining said second pressing force correction $\Delta PF_{set\text{-}ph}$ with said new desired pressing force $PF_{set}$ to form another new desired pressing force $PF_{set}$;

calculating another new pressing force deviation $\Delta PF$ between said another new desired pressing force $PF_{set}$ and said $PF_{actual}$;

operating said path height control circuit with said another new pressing force deviation $\Delta PF$ to calculate a new change in path height $\Delta PH$;

alternately repeating above steps A and B, and with each step using said new desired pressing force $PF_{set}$ from a previous said step as said desired pressing force $PF_{set}$.

10. A process in accordance with claim 9, wherein:

said calculating in said dosage control circuit of said change in dosage $\Delta D$ is by a pressing force to dosage sensitivity dPF/dD;

said calculating in said path height control circuit of said change in path height $\Delta PH$ is by a pressing force to path height sensitivity dPF/dD;

said calculating of said first pressing force correction $\Delta PF_{set\text{-}w}$ is by a weight to pressing force sensitivity dW/dPF;

said calculating of said height correction $K_T$ is by a height to pressing force sensitivity dT/dPF;

said calculating of said hardness correction $K_H$ is by a hardness to pressing force sensitivity dH/dPF.

11. A process in accordance with claim 10, wherein:

said dPF/dD, said dPF/dD, said dPF/dW, said dPF/dT, and said dPF/dH are continuously adapted to changing behavior of the press.

12. A process in accordance with claim 9, wherein:

said actual values of said height, said hardness and said weight of the tablets are assigned to an individual pressing station of the press.

13. A process in accordance with claim 9, wherein:

limit values for said pressing force are adaptively adjusted to preset limit values for said weight, said height and said hardness.

14. A process in accordance with claim 9, wherein:

FUZZY logic methods are used for said calculations of said change in dosage $\Delta D$, said change in path height $\Delta PH$, said first pressing force correction $\Delta PF_{set\text{-}w}$, said height correction $K_T$, and said hardness deviation $\Delta H$.

* * * * *